US00PP24843P2

(12) United States Plant Patent
Korlipara

(10) Patent No.: US PP24,843 P2
(45) Date of Patent: Sep. 2, 2014

(54) ***EUPATORIUM* PLANT NAMED 'CAPRI'**

(50) Latin Name: *Eupatorium fortunei*
Varietal Denomination: Capri

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 61 days.

(21) Appl. No.: 13/815,313

(22) Filed: Feb. 19, 2013

(51) Int. Cl.
*A01H 5/00* (2006.01)

(52) U.S. Cl.
USPC ..... Plt./263.1

(58) Field of Classification Search
CPC ..... A01H 5/02; A01H 1/00; A01H 1/02; A01H 1/04; A01H 3/00; A01H 3/04; A01H 4/005
USPC ..... Plt./263.1
See application file for complete search history.

*Primary Examiner* — Annette Para
(74) *Attorney, Agent, or Firm* — Klarquist Sparkman, LLP

(57) ABSTRACT

A new and distinct form of *Eupatorium* plant characterized by leaves variegated grey green with creamy margins, a very stable leaf variegation, a low, upright habit, growing from 2 to 2½ feet tall, and excellent vigor.

1 Drawing Sheet

Botanical denomination: *Eupatorium fortunei.*
Variety designation: 'Capri'.

BACKGROUND OF THE INVENTION

The present invention relates to a new and distinct cultivar of *Eupatorium fortunei*, given the name, 'Capri'. *Eupatorium* is in the family Asteraceae. This dwarf form was found as a whole plant mutation in the tissue culture lab in Canby, Oreg. It stood out as an extremely compact form.

Compared to the parent plant, *Eupatorium fortunei* 'Pink Frost' (syn. 'Pink Elegance'), an unpatented plant, the new cultivar is much shorter and has a more stable variegation.

Compared to *Eupatorium fortunei* 'Frosted Elegance', US Plant Patent applied for, the new cultivar is much shorter.

SUMMARY OF THE INVENTION

*Eupatorium* 'Capri' is uniquely distinguished by:

1. leaves variegated grey green with creamy margins,
2. a very stable leaf variegation,
3. a low, upright habit, growing from 2 to 2½ feet tall, and
4. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a ten-month-old *Eupatorium* 'Capri' growing in the trial field in full sun in October in Canby, Oreg.

FIG. 2 shows a close up of a flower.

DETAILED PLANT DESCRIPTION

The following is a detailed description of the new *Eupatorium* cultivar based on observations of ten-month-old specimens grown outside in the trial field in full sun in Canby, Oreg. in October. The color descriptions are all based on The *Royal Horticultural Society Colour Chart,* 5$^{th}$ edition.

Plant:

*Type*.—Perennial to subshrub.
*Form*.—Upright.
*Cold hardiness*.—USDA Zone 4-9.
*Size*.—Grows to 38 cm wide and 53 cm high.
*Vigor*.—Excellent.
*Stem*.—Grows to 42 cm long and 6 mm wide, with internodes 1.5 cm to 4 cm long, pubescent except where woody at the base, Yellow Green 147C in shade to Brown 200A in sun and at the base.
*Rooting*.—Roots easily from soft wood cuttings.

Leaf:

*Type*.—Simple.
*Arrangement*.—Opposite.
*Shape*.—Lower leaves ovate overall and deeply 3 cleft with terminal segments oblong or oblong lanceolate and lateral lobes lanceolate to elliptic; upper leaves lanceolate to elliptic and 0 to 3 lobed.
*Margins*.—Serrate.
*Venation*.—Pinnate, Yellow Green 147D on top side and 147C on bottom.
*Apex*.—Acute to acuminate.
*Base*.—Cuneate.
*Blade size*.—Grows to 8.5 cm long and 5 cm wide.
*Surface texture*.—Glabrous on top, pubescent on bottom.
*Petiole*.—Grows to 1 mm to 7 mm long and 1.3 mm wide, sparsely pubescent, Yellow Green 147B sometimes tinted Greyed Purple 187B on topside.
*Fragrance*.—None.

*Leaf color*.—Topside Yellow 2D on margins with centers irregularly blotched Yellow Green 147B and with tints of Greyed Purple 183B under stress or cool temperatures.

Inflorescence:

*Type*.—Dense corymb.

*Size*.—Grows to 7 mm deep and 3.5 mm wide.

*Peduncle*.—Grows to 3 cm long, 2 mm wide, pubescent, Yellow Green 147B tinted Greyed Purple 183B in sun.

*Immature heads*.—Cylindrical, 1.5 mm wide and 4 mm deep, Red Purple 64A, glabrous.

*Receptacle*.—Disc shaped, 3 mm wide and 1.5 mm deep, Green 136D.

*Involucral bracts*.—About 10, 2- or 3-seriate, 2.5 mm long and 1 mm wide, elliptic, tip and base obtuse, margin entire, pubescent on margins, glabrous and Red Purple 64A both sides.

*Lastingness*.—Each inflorescence lasts about two weeks on the plant.

Florets:

*Type*.—Composite with 2 to 5 florets per head.

*Ray florets*.—None.

*Disc florets*.—Tubular, with stamen and pistil, about 4 in number, 7 mm long and 2 mm wide; corolla regular, 4.5 mm long and 2 mm wide, 5 lobed, lower ⅔ Greyed Purple 186C, top ⅓ including lobes White N155B; pistil 1, 6 mm long, ovary 1.5 mm long, Greyed Purple 182C, style 4 mm long, with extruding, 2-branched stigma spreading 10 mm wide, style and stigma White N155B; stamen 5, anthers 1.5 mm long, Greyed Purple N187A, pollen none seed.

*Bloom period*.—August through frost in Canby, Oreg.

*Fragrance*.—None.

*Seed*.—None seen.

*Fertility*.—Unknown.

Disease and pests: No pests or diseases have been observed on plants grown under commercial conditions in Canby, Oreg. No resistances are known.

I claim:

1. A new and distinct form of *Eupatorium* plant as shown and described.

* * * * *

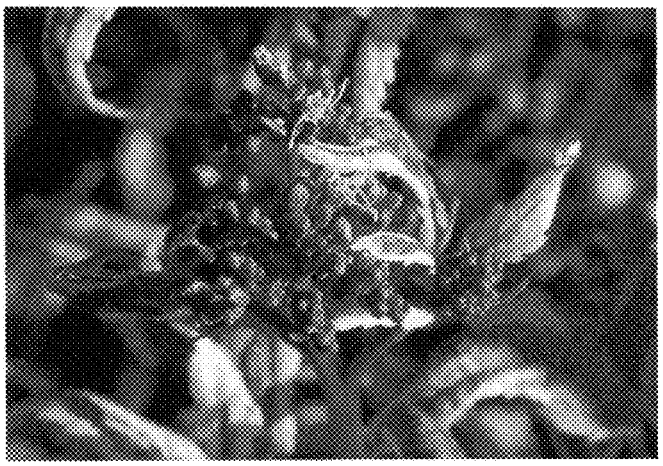

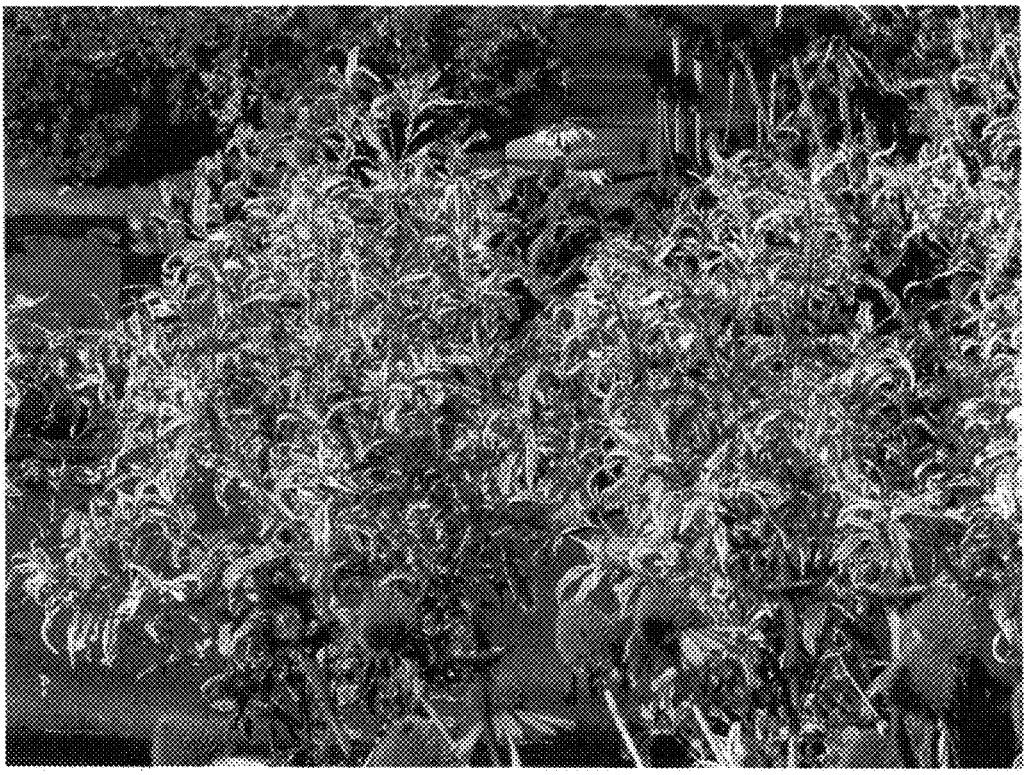
FIG. 1 above, FIG. 2 below